US005593983A

United States Patent [19]
Campbell

[11] Patent Number: 5,593,983
[45] Date of Patent: Jan. 14, 1997

[54] SUBSTITUTED 2β-MORPHOLINO-ANDROSTANE DERIVATIVES

[75] Inventor: Alexander C. Campbell, Falkirk, Scotland

[73] Assignee: Akzo Nobel N.V., Arnhem, Netherlands

[21] Appl. No.: 347,974

[22] Filed: Dec. 1, 1994

[30] Foreign Application Priority Data

Dec. 2, 1993 [EP] European Pat. Off. .............. 93309663

[51] Int. Cl.$^6$ .............................. A61K 31/58; C07J 43/00
[52] U.S. Cl. ............................................. 514/176; 540/95
[58] Field of Search ................................ 540/95; 514/176

[56] References Cited

U.S. PATENT DOCUMENTS

| | | | |
|---|---|---|---|
| 3,225,034 | 12/1965 | Hewett et al. | 540/95 |
| 3,553,212 | 1/1971 | Hewett et al. | 540/95 |
| 3,714,352 | 1/1973 | Davis et al. | 424/243 |
| 3,781,435 | 12/1973 | Davis et al. | 424/243 |
| 3,816,624 | 6/1974 | Davis et al. | 424/239 |
| 3,872,091 | 3/1975 | Hewett et al. | 540/95 |
| 3,983,111 | 9/1976 | Phillips et al. | 540/95 |
| 4,447,425 | 5/1984 | Carlyle et al. | 424/241 |
| 4,891,366 | 1/1990 | Sliegh et al. | 514/176 |
| 4,894,369 | 1/1990 | Sleigh et al. | 514/176 |
| 5,416,079 | 5/1995 | Campbell | 514/176 |

FOREIGN PATENT DOCUMENTS

| | | |
|---|---|---|
| 1377608 | 12/1974 | United Kingdom . |
| 1376892 | 12/1974 | United Kingdom . |
| 1380248 | 1/1975 | United Kingdom . |
| 1430932 | 4/1976 | United Kingdom . |
| 1570394 | 7/1980 | United Kingdom . |
| 1581234 | 12/1980 | United Kingdom . |

OTHER PUBLICATIONS

G. H. Phillipps, "Structure Activity Relationships in Steroidal Anaesthetics," *Molecular Mechanisms in General Anaesthesia*, 1974, pp. 32–47, London, GB.
G. H. Phillipps, "Structure Activity Relationships in Steroidal Anaesthetics," *Journal of Steroid Biochemistry*, vol. 6, No. 5, pp. 607–613, 1975, Oxford, GB.
A. Hassner et al., *Journal of Organic Chemistry*, 32:3, Mar. 1967, pp. 549–553.
G. H. Phillipps, *Mol. Rech. Gen. Anaesth.*, pp. 32–47, 1973.

*Primary Examiner*—Matthew V. Grumbling
*Attorney, Agent, or Firm*—Mary E. Gormley

[57] ABSTRACT

The invention is related to substituted 2β-morpholino-androstane derivatives, bonded at their 2β-position to the nitrogen of a group of formula I

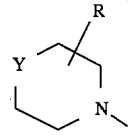

wherein R represents one to four substituents, each one independently selected from (1–4C) alkyl, phenyl and benzyl, or two at the same carbon atom being together —(CH$_2$)$_n$— wherein n is 2–6; and Y is O or S, or a pharmaceutically acceptable salt thereof. These steroids are very potent intravenous anaesthetics. The compounds have fast onset times and ideal 'sleep duration' vs. 'recovery to full coordination' profiles.

16 Claims, No Drawings

1
SUBSTITUTED 2β-MORPHOLINO-ANDROSTANE DERIVATIVES

FIELD OF THE INVENTION

The invention relates to substituted 2β-morpholino-androstane derivatives, a process for the preparation thereof, a pharmaceutical composition containing the same, as well as the use of these steroids as an anaesthetic drug.

BACKGROUND OF THE INVENTION

Androstanes are steroids having a skeleton of the formula hexadecahydro-10,13-dimethyl-1H-cyclopenta[a]-phenanthrene. The compounds with only a 13-methyl group are named 19-norandrostanes. Androstanes with an ethyl sidechain at the 17-position are named pregnanes. For reasons of simplicity only the term androstane is used in this description. The term androstane may, however, also be read as 19-norandrostane, pregnane, or 19-norpregnane. In the experimental section the usual chemical names are used.

Derivatives of androstane having intravenous anaesthetic activity are known in the art. They have less side effects when compared with other steroidal anaesthetics. These steroids may carry substituents at several positions (see for example British patents 1,376,892, 1,380,248, 1,430,932, 1,570,394, 1,377,608, and 1,581,234; and U.S. Pat. No. 3,983,111). A well-known example is alfaxalone as disclosed in German patent 2,030,402.

It has been found these steroids when substituted by various groups may have advantageous properties, but substitution may also lead to decrease of anaesthetic activity.

It is of particular advantage to have water soluble anaesthetic compounds, since such compounds can advantageously be used for intravenous anaesthesia. Anaesthetic androstane derivatives having groups which improve the water solubility at various positions of the steroid skeleton, are known. Introduction of such groups does not always lead to increase of activity or stability. In the search for water-soluble anaesthetic androstane derivatives having intravenous activity, 2β-amino-derivatives, and particularly 2β-morpholino derivatives were claimed to be favourable. Androstane derivatives having a morpholino group attached at the 2β-, 11α- or 21-positions of the steroid are disclosed as compounds with anaesthetic activity, for example in British patents 1,377,608 and 1,581,234, and in U.S. Pat. No. 3,983,111. However, the 2β-morpholino derivative of alfaxalone is significantly less active than alfaxalone itself.

SUMMARY OF THE INVENTION

It has now been found that substituted 2β-morpholino-androstane derivatives, the morpholino group of which is substituted by alkyl, spirocycloalkyl, phenyl, or benzyl, are very potent anaesthetic compounds having in general a better therapeutic index than the corresponding analogues containing an unsubstituted morpholino group. Furthermore, the compounds of the invention have fast onset times and ideal 'sleep duration' vs. 'recovery to full coordination' profiles.

In addition to anaesthetic activity, the compounds of the invention can be used for sedation and analgesia and for the treatment of GABA related diseases, such as anxiety (for instance panic attack), stress, sleep disorders, post natal depression, and premenstrual tension, and for the alleviation of seizure.

DETAILED DESCRIPTION OF THE INVENTION

The invention relates to substituted 2β-morpholino-androstane derivatives, bonded at their 2β-position to the nitrogen of a group of formula I:

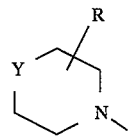

wherein R represents one to four substituents, each one independently selected from (1–4C) alkyl, phenyl and benzyl, or two at the same carbon atom being together —$(CH_2)_n$— wherein n is 2–6; and Y is O or S; or a pharmaceutically acceptable salt thereof.

Preferred compounds according to this invention are androstane derivatives of formula II:

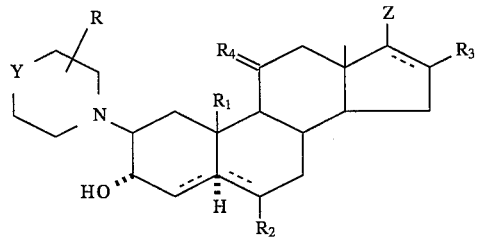

wherein R represents one to four substituents, each one independently selected from (1–4C) alkyl, phenyl and benzyl, or two at the same carbon atom being together —$(CH_2)_n$— wherein n is 2–6; $R_1$, $R_2$, and $R_3$ are independently H or methyl; $R_4$ is $H_2$, (H,OH) or O; Z is CN or CO—$CH_2$X;

X is selected from H, halogen, OH, CN, $N_3$, SCN, (1–6C) alkyl (optionally substituted by halogen), cyclohexyl, (1–6C) alkoxy, phenoxy, phenyl-(1–6C) alkoxy, (1–6C) acyloxy, (1–6C) acylthio, pyrrolidinyl, piperidinyl, morpholinyl, thiomorpholinyl and amino which is optionally substituted by (1–6C) alkyl; Y is O or S; and the dotted lines are optional bonds, H(5) being absent when the 4,5- or 5,6-linkage is a double bond; or a pharmaceutically acceptable salt thereof.

Particularly useful compounds according to the invention are steroids of the formula III:

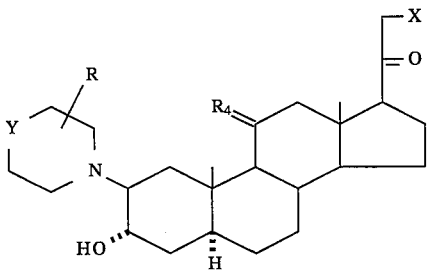

wherein R, $R_4$, X and Y have the previously given meanings; or a pharmaceutically acceptable salt thereof.

Preferred compounds are steroids of the invention wherein R represents one or two methyl groups. More preferred compounds have two methyl groups at the 2-position of the morpholino (morpholinyl) moiety.

Other preferred compounds are steroids of formula III wherein $R_4$ is O. Also preferred are steroid derivatives of formula III wherein X is H, Cl, OH, CN, $N_3$, SCN, (1–6C) acyloxy or (1–6C) acylthio, and Y is O.

Most preferred is the steroid having formula IV:

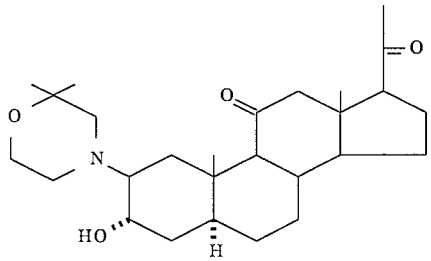

a pharmaceutically acceptable salt thereof.

The term morpholine (and terms derived therefrom) is used for morpholine as well as for thiomorpholine.

The term (1–6C) alkyl used in the definition of X means a branched or unbranched alkyl group having 1–6 carbon atoms, for example methyl, ethyl, propyl, isopropyl, butyl, sec-butyl, tert-butyl, pentyl, neopentyl or hexyl.

The term (1–4C) alkyl means methyl, ethyl, propyl, isopropyl, butyl, sec-butyl, isobutyl, or tert-butyl.

The term acyl as used in (1–6C) acyloxy and (1–6C) acylthio, means a 1-oxo-alkyl having 1–6 carbon atoms.

The term (1–6C) alkoxy means alkyloxy having 1–6 carbon atoms, wherein alkyl has the same meaning as previously given for the (1–6C) alkyl group.

The term halogen means fluoro, chloro, bromo or iodo.

In the term —$(CH_2)_n$— n is 2 (spirocyclopropane) to 6 (spirocycloheptane). Preferably n is 4 or 5, and most preferred n is 5.

The substituted 2β-morpholino-androstane derivatives of the invention can be prepared by methods commonly known in the art.

A general method is condensation of a suitably substituted morpholine to the 2β-position of an androstane derivative by bringing together the substituted morpholine (or thiomorpholine) or a salt thereof and a 2,3-epoxy-androstane or 2,3-epoxy-19-norandrostane derivative, which is suitably protected when necessary. After removal of the optionally present protective groups, the steroid obtained is isolated and purified by procedures well known in the art, followed, when required, by the introduction of a substituent at the 21-position of the steroid.

2,2-Disubstituted morpholine derivatives are prepared by either condensation of 2-aminoethanol and an appropriate 2-chloro-1,1-dialkylethanol, or by addition of 2-aminoethanol to an appropriate 2,2-dialkyloxirane. The resulting N-(2, 2-dialkyl-2-hydroxyethyl)-N-(2-hydroxyethyl)amine is subsequently protected, for example by treatment with tosylchloride in pyridine to obtain N-(2,2-dialkyl-2-hydroxyethyl)-N-[(4-methylphenyl)sulfonyl]-N-[2-[(4-methylphenyl)sulfonyloxy]ethyl]amino, cyclized, and N-deprotected to obtain the required substituted morpholine derivative.

Other substituted morpholine derivatives can be prepared according to literature procedures (G. R. Brown et al., J. Pharm. Pharmacol., 1990, 42, 797; G. Bettoni et al., Tetrahedron, 1980, 36, 409).

The substituted morpholino moiety may contain one or more chiral carbon atoms, and the compounds may therefore be obtained as pure stereoisomers, or as a mixture of stereoisomers. Methods for obtaining the pure stereoisomers are well known in the art, e.g. by synthesis with chiral induction, crystallisation, or by chromatography.

The compounds of the invention may be converted into a pharmaceutically acceptable salt by treating the free base with a pharmaceutically acceptable organic or inorganic acid such as HCl, HBr, HI, $H_2SO_4$, $H_3PO_4$, acetic acid, propionic acid, glycolic acid, maleic acid, malonic acid, methanesulfonic acid, fumaric acid, succinic acid, tartaric acid, citric acid, benzoic acid, and ascorbic acid.

In Table I the therapeutic index of compounds of the invention is compared with the therapeutic index of corresponding analogues comprising an unsubstituted morpholinyl group. The therapeutic index (T.I.) is defined as the ratio of the lethal dose in 50% of the animals ($LD_{50}$) and the hypnotic dose ($HD_{50}$), which is the dose of the compound which, following intravenous administration over 10 sec, causes a loss of righting reflex in of the animals for a period of no less than 30 sec.

TABLE I

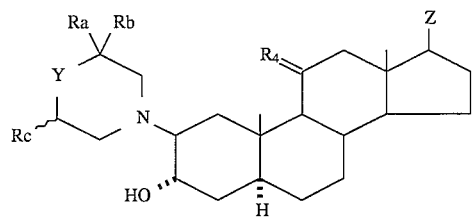

| $R_a$ | $R_b$ | $R_c$ | $R_4$ | Z | Y | T.I. Mouse |
|---|---|---|---|---|---|---|
| # H | H | H | 2H | $COCH_3$ | O | 4.3 |
| $CH_3$ | $CH_3$ | H | 2H | $COCH_3$ | O | 9.4 |
| H | H | (R)—$CH_3$ | 2H | $COCH_3$ | O | 8.3 |
| H | H | (S)—$CH_3$ | 2H | $COCH_3$ | O | 4.9 |
| H | H | (R)—$C_2H_5$ | 2H | $COCH_3$ | O | 5.7 |
| H | H | (S)—$C_2H_5$ | 2H | $COCH_3$ | O | 6.6 |
| H | H | (R)—$CH_2Ph$ | 2H | $COCH_3$ | O | 5.0 |
| H | H | (S)—$CH_2Ph$ | 2H | $COCH_3$ | O | 4.8 |
| $CH_3$ | H | $CH_3$(cis) | 2H | $COCH_3$ | O | 6.2 |
| $CH_3$ | $CH_3$ | H | 2H | $COCH_2SCN$ | O | 4.0 |
| H | H | (R)—$CH_3$ | 2H | $COCH_2Cl$ | O | 6.2 |
| $CH_3$ | $CH_3$ | H | 2H | CN | O | 8.5 |
| #H | H | H | 2H | $COCH_2OH$ | O | 4.9 |
| $CH_3$ | $CH_3$ | H | 2H | $COCH_2OH$ | O | 9.6 |
| #H | H | H | 2H | $COCH_2OAc$ | O | 3.6 |
| $CH_3$ | $CH_3$ | H | 2H | $COCH_2OAc$ | O | 8.6 |
| #H | H | H | O | $COCH_2Cl$ | O | conv. |
| $CH_3$ | $CH_3$ | H | O | $COCH_2Cl$ | O | 7.8 |
| $CH_3$ | $CH_3$ | H | O | $COCH_2SCN$ | O | 4.4 |
| $CH_3$ | $CH_3$ | H | O | $COCH_2N_3$ | O | <11 |
| $CH_3$ | $CH_3$ | H | O | $COCH_2CN$ | O | 6.7 |
| #H | H | H | O | $COCH_2SAc$ | O | 5.6 |
| $CH_3$ | $CH_3$ | H | O | $COCH_2SAc$ | O | 11.2 |
| $CH_3$ | $CH_3$ | H | O | $COCH_2OAc$ | O | 11.6 |
| #H | H | H | O | $COCH_3$ | O | 4.4 |
| $CH_3$ | $CH_3$ | H | O | $COCH_3$ | O | 13.4 |
| $CH_3$ | H | $CH_3$(cis) | O | $COCH_3$ | O | 5.8 |
| H | H | (R)—$CH_3$ | O | $COCH_3$ | O | 5.4 |
| H | H | (R)—$C_2H_5$ | O | $COCH_3$ | O | 5.8 |
| H | H | (S)—$C_2H_5$ | O | $COCH_3$ | O | 8.1 |
| $C_4H_9$ | $C_4H_9$ | H | O | $COCH_3$ | O | 3.8 |
| Ph | Ph | H | O | $COCH_3$ | O | >3.3 |
| H | H | (R)—$CH_2Ph$ | O | $COCH_3$ | O | 6.3 |
| H | H | (S)—$CH_2Ph$ | O | $COCH_3$ | O | 6.9 |
| $C_2H_5$ | $C_2H_5$ | H | O | $COCH_3$ | O | 7 |
| —$(CH_2)_5$— | | H | O | $COCH_3$ | O | 8.3 |
| $CH_3$ | $CH_3$ | $CH_3,CH_3$* | O | $COCH_3$ | O | 15.4 |
| $CH_3$ | $CH_3$ | H | 2H | $COCH_3$ | S | 3.7 |
| $CH_3$ | $CH_3$ | H | O | $COCH_3$ | S | 16.3 |
| #H | H | H | O | CN | O | 5.9 |
| $CH_3$ | $CH_3$ | H | O | CN | O | 10.3 |

# = reference compound; conv. = convulsive; Ac = acetyl; Ph = Phenyl; * = two substituents $R_c$.

The compounds of the invention may be administered parenterally, and for humans preferably in a dosage of 0.001–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8, Chapters 84 and 85: Parenteral Preparations and Intravenous Admixtures), the compounds may by means of pharmaceutically suitable liquids be applied as an injection preparation in the form of a solution, suspension, or emulsion. Pharmaceutically acceptable additives, such as colorants, which do not interfere with the function of the active compounds, can be used for making dosage units. The compounds are preferably administered intravenously.

The invention is further illustrated by the following examples.

General: Unless otherwise stated optical rotations were measured in chloroform at room temperature. c is concentration in g/100 ml.

EXAMPLE 1

(2β,3α,5α)-3-hydroxy-2-(2,2-dimethyl-4-morpholinyl)pregnane-11,20-dione 2,2-Dimethylmorpholine hydrochloride 1-Chloro-2-methyl-2-propanol (135 ml) was added dropwise over 10 min to stirred 2-aminoethanol (400 ml) at 10° C. under nitrogen. The cooling bath was then removed and stirring was continued at room temperature for 48 h. A solution of sodium hydroxide (48.8 g) in methanol (440 ml) was added and the resulting white suspension was stirred for 10 min. The mixture was filtered through a pad of kieselguhr and the filtrate was concentrated under reduced pressure. The residual oil was distilled in vacuo to give 1-[(2-hydroxyethyl)amino]-2-methyl-2-propanol (133 g). b.p. 100°–108° C. (1.5 mm Hg).

4-Toluenesulfonyl chloride (166.1 g) was added portionwise to a stirred solution of 1-[(2-hydroxyethyl)amino]-2-methyl-2-propanol (58.0 g) in pyridine (275 ml) at 0°–10° C. The resulting solution was stirred at room temperature for 15 h and then poured into water (1 l). The mixture was extracted with dichloromethane and the organic phase was washed with hydrochloric acid (2.5M) and brine. After drying over magnesium sulfate, the solvent was removed under reduced pressure to give 1-{N-[(4-methylphenyl)sulfonyl]-N-[(4-methylphenyl)sulfonyloxyethyl]amino}-2-methyl-2-propanol (155.8 g). δ (CDCl$_3$) 1.23 (s,6H), 2.44,2.46 (6H), 3.08 (s,2H), 3.45 (t,2H), 4.35 (t,2H) and 7.25–7.85 (m,8H).

Sodium methoxide (9.7 g) was added to a stirred solution of 1-{N-[(4-methylphenyl)sulfonyl]-N-[(4-methylphenyl)sulfonyloxyethyl]amino}-2-methyl-2-propanol (72.2 g) in methanol (350 ml) and the solution was stirred at room temperature for 1.5 h. A further amount of sodium methoxide (9.7 g) was then added and the mixture was stirred for an additional 30 min. The suspension was poured into water (1.2 l) and the mixture was stirred for 20 min. The colourless solid was filtered off, washed with water and dried in vacuo at 60° C. to give 2,2-dimethyl-4-[(4-methylphenyl)sulfonyl]morpholine (41.0 g). m.p. 95°–97° C.

Sodium (24.0 g) was added portionwise over 1.25 h to a stirred solution of 2,2-dimethyl-4-[(4-methylphenyl)sulfonyl]morpholine (25.0 g) in 1-pentanol (250 ml) at 70° C. in an atmosphere of nitrogen and the mixture was heated under reflux for 1 h. After the addition of another quantity of 1-pentanol (100 ml), the solution was distilled under reduced pressure and a mixture of the product and 1-pentanol was collected in a receiver immersed in a cooling bath. This distillate was acidified by addition of a solution of dry hydrogen chloride in methanol. The solvent was removed under reduced pressure and the product was crystallised from a mixture of methanol and diethyl ether (1:5 v/v) to afford 2,2-dimethylmorpholine hydrochloride (1:1) salt (12.4 g). m.p. 136°–137° C.

2,2-Dimethylmorpholine hydrochloride (806 g) and powdered sodium hydroxide (212 g) were added to a stirred mixture (3.5:1) of (2α,3α,5α)-2,3-epoxypregnane-11,20-dione 20-cyclic 1,2-ethanediyl acetal and its 3α,4α-epoxy isomer (500 g) (prepared as described in British Patent 1,039,441) in 1,2-ethanediol (5 l). The mixture was heated at 113° C. and then poured into water (30 l). The precipitated solid was filtered off, washed with water and suspended in water (2.5 l). A solution of methanesulfonic acid (204 ml) in water (500 ml) was added and the mixture was stirred at room temperature for 1 h and then filtered. The filtrate was extracted with ethyl acetate and the aqueous phase was adjusted to pH 9 with aqueous sodium hydroxide (4M). The precipitated solid was filtered off, dried in vacuo and then crystallised twice from acetone-hexane to give (2β,3α,5α)-3-hydroxy-2-(2,2-dimethyl-4-morpholinyl)pregnane-11,20-dione (294 g). m.p. 163° C.; [α]$_D$ +128° (c 1.1).

EXAMPLE 2

(2β,3α,5α)-21-chloro-3-hydroxy-2-(2,2-dimethyl-4-morpholinyl)pregnane-11,20-dione The (2β,3α,5α)-3-hydroxy-2-(2,2-dimethyl-4-morpholinyl)pregnane-11,20-dione (8.0 g), 2-aminoethanol (40 ml), toluene (200 ml) and Dowex 50-W resin (0.8 g) were added to a flask fitted with a water separator. The mixture was heated under reflux for 10 h, by which time approximately 15 ml of a distillate had collected in the water separator. The contents of the flask were filtered while still hot and the residue was rinsed with hot toluene. The filtrate was washed with water, dried over sodium sulfate and the solvent was removed under reduced pressure to give (2β,3α,5α)-3-hydroxy-20-[(2-hydroxyethyl)imino]-2-(2,2-dimethyl-4-morpholinyl)pregnan-11-one. δ (CDCl$_3$) 0.50 (s,3H), 1.05 (s,3H), 1.21 (s,3H), 1.23 (s,3H) and 2.36 (s,2H).

N-Chlorosuccinimide (2.16 g) was added to a solution of (2β,3α,5α)-3-hydroxy-20-[(2-hydroxyethyl)imino]-2-(2,2-dimethyl-4-morpholinyl)pregnan-11-one (8.77 g) in tetrahydrofuran (175 ml). The solution was stirred at room temperature for 2 h and hydrochloric acid (53 ml; 1M) was then added. After stirring at room temperature for 1.25 h, the reaction mixture was poured into water (1 l). The pH was adjusted to 9 with aqueous sodium carbonate and the precipitated solid was filtered off, washed with water and dissolved in dichloromethane. After drying over sodium sulfate, the solvent was removed under reduced pressure and the residue was chromatographed on silica gel. The purified product was crystallised from diethyl ether to give (2β,3α,5α)-21-chloro-3-hydroxy-2-(2,2-dimethyl-4-morpholinyl)pregnane-11,20-dione (3.23 g). m.p. 206°–208° C. (dec); [α]$_D$ +130.5° (c 0.57).

EXAMPLE 3

(2β,3α,5α)-(acetylthio)-3-hydroxy-2-(2,2-dimethyl-4-morpholinyl)pregnane-11,20-dione Potassium thioacetate (1.32 g) was added to a solution of the 21-chloro-compound of Example 2 (2.22 g) in ethanol (11.1 ml). The mixture was heated under reflux in an atmosphere of nitrogen for 40 min and then poured into water (100 ml). The precipitated solid was filtered off, washed with water and dissolved in dichloromethane. After drying the solution over sodium sulfate the solvent was removed under reduced pressure and the residue was chromatographed on silica gel. The purified product was crystallised from methanol to give (2β,3α,5α)-21-(acetylthio)-3-hydroxy-2-(2,2-dimethyl-4-morpholinyl)pregnane-11,20-dione (1.46 g). m.p. 181°–182° C.; [α]$_D$ +131.9° (c 0.88).

EXAMPLE 4

(2β,3α,5α)-21(acetyloxy)-3-hydroxy-2-(2,2-dimethyl-4-morpholinyl)pregnane-11,20-dione Potassium acetate (0.83 g) was added to a solution of the 21-chloro compound of Example 2 (0.5 g), potassium iodide (0.04 g), glacial acetic acid (1.05 ml) and N,N-dimethylformamide (20 ml) and the mixture was heated at 65° C. in an atmosphere of nitrogen for 1.5 h. The mixture was then poured into water (200 ml) and aqueous sodium carbonate was added until the pH exceeded 9. The precipitated solid was filtered off, washed with water and dissolved in dichloromethane. After drying over sodium sulfate, the solvent was removed under reduced pressure and the residue was crystallised from methanol to give (2β,3α,5α)-21-(acetyloxy)-3-hydroxy-2-(2,2-dimethyl-4-morpholinyl)pregnane-11,20-dione (0.33 g). m.p. 158°–160° C.; [α]$_D$ +123° (c 0.68).

EXAMPLE 5

(2β,3α,5α)-3-hydroxy-2-(cis-2,6-dimethyl-4-morpholinyl)pregnane-11,20-dione

A mixture of cis- and trans-2,6-dimethylmorpholine (60 ml) was added to a stirred mixture (3.5:1) of (2α,3α,5α)-2,3-epoxypregnane-11,20-dione 20-cyclic 1,2-ethanediyl acetal and its 3α,4α-epoxy isomer (9.0 g) (prepared as described in British patent 1,039,441) in 1,2-ethanediol (180 ml). The mixture was heated at 125° C. for 2.5 h and then poured into water (1.8 l). The precipitated solid was filtered off, washed with water and dissolved in methanol (150 ml). Methanesulfonic acid was then added until the pH was less than 7 and this solution was stirred at room temperature for 1 h and then poured into water (1 l). The mixture was extracted with diethyl ether and sodium carbonate was then added to the aqueous phase until the pH exceeded 9. The resulting mixture was extracted with diethyl ether and the organic phase was washed with water and dried over sodium sulfate. The solvent was removed under reduced pressure and the residue was chromatographed on silica gel. The purified product was crystallised from methanol to give (2β,3α,5α)-3-hydroxy-2-(cis-2,6-dimethyl-4-morpholinyl)pregnane-11,20-dione (0.87 g). m.p. 172.5°–174.5° C.; [α]$_D$ +142.5° (c 0.54).

EXAMPLE 6

(2β,3α,5α)-3-hydroxy-3-hydroxy-2-(2,2-dimethyl-4-morpholinyl)pregnane-11,20-dione 2-hydroxy-1,2,3-propanetricarboxylate (1:1) salt A solution of citric acid (368 mg) in methanol (4 ml) was added to a solution of (2β,3α,5α)-3-hydroxy-2-(2,2-dimethyl-4-morpholinyl)pregnane-11,20-dione of Example 1 (854 mg) in methanol (6 ml). The solvent was removed under reduced pressure to give (2β,3α,5α)-3-hydroxy-2-(2,2-dimethyl-4-morpholinyl)-pregnane-11,20-dione 2-hydroxy-1,2,3-propanetricarboxylate (1:1) salt (1.22 g). [α]$_D$ +96.6° (c 1.03).

In a similar manner the following salts were prepared:

(i) With the 21-chloro compound of Example 2 and methanesulfonic acid as starting materials, (2β,3α,5α)-21-chloro-3-hydroxy-2-(2,2-dimethyl-4-morpholinyl)-pregnane-11,20-dione methanesulfonate (1:1) salt was formed. [α]$_D$ +104.3° (c 1.20).

(ii) With the 21-(acetylthio) compound of Example 3 and methanesulfonic acid as starting materials, (2β,3α,5α)-21-(acetylthio)-3-hydroxy-2-(2,2-dimethyl-4-morpholinyl)pregnane-11,20-dione methanesulfonate (1:1) salt was formed. [α]$_D$ +110° (c 0.8).

(iii) With the 21-(acetyloxy) compound of Example 4 and methanesulfonic acid as starting materials, (2β,3α,5α)-21-(acetyloxy)-3-hydroxy-2-(2,2-dimethyl-4-morpholinyl)pregnane-11,20-dione methanesulfonate (1:1) salt was formed. [α]$_D$ +99.4° (c 0.81).

(iv) With the cis-2,6-dimethyl-4-morpholinyl compound of Example 5 and citric acid as starting materials, (2β,3α,5α)-3-hydroxy-2-(cis-2,6-dimethyl-4-morpholinyl)pregnane-11,20-dione 2-hydroxy-1,2,3-propanetricarboxylate (1:1) salt was formed. [α]$_D$ +100.5° (c 1.09).

EXAMPLE 7

(2β,3α,5α)-3,21-dihydroxy-2-(2,2-dimethyl-4-morpholinyl)pregnane-11,20-dione

Acetyl chloride (9.71 ml) was added to a stirred solution of (3β,5α)-3-hydroxypregnane-11,20-dione (97.1 g) [prepared as described by Cameron et al., J. Chem. Soc., 1955, 2807] in methanol (2.4 l) and a solution of bromine (18.5 ml) in methanol (1 l) was then added over 30 min at room temperature. The reaction mixture was poured into water (30 l) and the precipitated solid was filtered off, washed with water and dissolved in dichloromethane. After drying the solution over sodium sulfate, the solvent was removed under reduced pressure to give crude (3β,5α)-21-bromo-3-hydroxypregnane-11,20-dione (120 g). δ (CDCl$_3$) 0.61 (s,3H), 1.02 (s,3H), 3.00–3.20 (m,1H), 3.49–3.62 (m,2H) and 3.85 (s,2H). Potassium acetate (240 g), potassium iodide (6 g) and glacial acetic acid (250 ml) were added to a solution of (3β,5α)-21-bromo-3-hydroxypregnane-11,20-dione (120 g) in acetone (4.8 l) and the mixture was heated under reflux for 3 h. The reaction mixture was poured into water (50 l) and the precipitated solid was filtered off, washed with water and dissolved in dichloromethane. After drying the solution over sodium sulfate, the solvent was removed under reduced pressure. The residue was chromatographed over silica gel and the purified product was crystallised from diethyl ether to give (3β,5α)-21-(acetyloxy)-3-hydroxypregnane-11,20-dione (26 g) m.p. 163°–165° C.; [α]$_D$ +103.3° (c 0.97). 4-Toluenesulfonyl chloride (52 g) was added to a solution of (3β,5α)-21-(acetyloxy)-3-hydroxypregnane-11,20-dione (26 g) in pyridine (260 ml) and the solution was stirred for 4 h at room temperature. The reaction mixture was poured into water (2.6 l) and the precipitated solid was filtered off, washed with water and dissolved in dichloromethane. After drying the solution over sodium sulfate, the solvent was removed under reduced pressure. Crystallisation of the residue from methanol gave (3β,5α)-21-(acetyloxy)-3-{[(4-methylphenyl)sulfonyl]oxy}pregnane-11,20-dione (35 g). m.p. 155°–156° C.; [α]$_D$ +62.4° (c 1.11).

A solution of (3β,5α)-21-(acetyloxy)-3-{[(4-methylphenyl)sulfonyl]oxy}pregnane-11,20-dione (35 g) in collidine (350 ml) was heated under reflux for 2 h. The reaction mixture was poured into water (3.5 l) containing hydrochloric acid (614 ml; 5M) and the precipitated solid was filtered off, washed with water and dissolved in dichloromethane. After drying the solution over sodium sulfate, the solvent was removed under reduced pressure. Crystallisation of the residue from methanol gave a mixture (3:1) (18.8 g) of (5α)-21-(acetyloxy)pregn-2-ene-11,20-dione and its 3-ene-isomer.

A solution of potassium carbonate in methanol (190 ml; 0.19M) was added to a suspension of (5α)-21-(acetyloxy)pregn-2-ene-11,20-dione and its 3-ene-isomer (18.8 g) in methanol (188 ml). The resulting solution was stirred at room temperature for 30 min and poured into water (3.7 l). The mixture was extracted with dichloromethane and the organic phase was washed with water, dried over sodium sulfate and the solvent was removed under reduced pressure. The residue was chromatographed on silica gel to give a mixture (3:1) (15.3 g) of (5α)-21-hydroxypregn-2-ene-11,20-dione and its 3-ene-isomer.

4-Toluenesulfonic acid (0.91 g) was added to a stirred mixture (3:1) of (5α)-21-hydroxypregn-2-ene-11,20-dione and its 3-ene-isomer (15.2 g) in 1,2-ethanediol (15 ml) and triethylorthoformate (30 ml) was added. The mixture was heated at 80° C. for 15 min and then poured into water (450 ml) containing sodium carbonate (0.83 g). The mixture was extracted with diethyl ether and the organic phase was washed with water, dried over sodium sulfate and the solvent was removed under reduced pressure. The residue was chromatographed on alumina to give a mixture (3:1) of (5α)-21-hydroxypregn-2-ene-11,20-dione 20-cyclic 1,2-ethanediyl acetal and its 3-ene-isomer (12.7 g).

To a stirred solution of the mixture (3:1) of (5α)-21-hydroxypregn-2-ene-11,20-dione 20-cyclic 1,2-ethanediyl acetal and its 3-ene-isomer (6.52 g) in dichloromethane (26 ml) was added a solution of 3-chloroperbenzoic acid (3.6 g) in dichloromethane (68 ml), maintaining the temperature below 25° C. The solution was stirred at room temperature for 1.5 h and potassium hydrogen carbonate (8.05 g) was added. Water (100 ml) was added and the organic phase was washed sequentially with water, sodium thiosulfate solution and water, and then dried over sodium sulfate. The solvent was removed under reduced pressure to give a mixture (3:1) of (2α,3α,5α)-2,3-epoxy-21-hydroxypregnane-11,20-dione 20-cyclic 1,2-ethanediyl acetal and its 3α,4α-epoxy isomer (6.8 g).

2,2-Dimethylmorpholine (9.2 g) was added to a stirred mixture (3:1) of (2α,3α,5α)-2,3-epoxy-21-hydroxypregnane-11,20-dione 20-cyclic 1,2-ethanediyl acetal and its 3α,4α-epoxy isomer (3.0 g) in 1,2-ethanediol (60 ml) and the mixture was heated under reflux for 3 h. The reaction mixture was poured into water (600 ml) and the precipitated solid was filtered off and washed with water. The solid was dissolved in methanol (100 ml) and a solution of methanesulfonic acid (3.0 g) in methanol (50 ml) was added. This solution was stirred at 50° C. for 1 h, concentrated in vacuo to ca. 50 ml and aqueous sodium carbonate was added until the pH exceeded 9. The mixture was extracted with dichloromethane and the organic phase was dried over sodium sulfate. The solvent was removed under reduced pressure and the residue was chromatographed on silica gel. The product was further purified via crystallisation of the oxalate salt. The free base was then regenerated by treatment with aqueous methanolic sodium carbonate. Crystallisation from acetone afforded (2β,3α,5α)-3,21-dihydroxy-2-(2,2-dimethyl-4-morpholinyl)pregnane-11,20-dione (227 mg). δ (CDCl$_3$) 0.60 (s,3H), 1.05 (s,3H), 1.23 (s,3H), 1.25 (s,3H) and 4.16 (s,2H).

EXAMPLE 8

(2β,3α,5α)-3,21-dihydroxy-2-(2,2-dimethyl-4-morpholinyl)pregnane-11,20-dione methanesulfonate (1:1) salt A solution of methanesulfonic acid (17.7 mg) in methanol (10 ml) was added to a solution of (2β,3α,5α)-3,21-dihydroxy-2-(2,2-dimethyl-4-morpholinyl)pregnane-11,20-dione (85 ml) in methanol (10 ml). The solvent was removed under reduced pressure to give (2β,3α,5α)-3,21-dihydroxy-2-(2,2-dimethyl-4-morpholinyl)pregnane-11,20-dione methanesulfonate (1:1) salt (103 mg). δ (CDCl$_3$) 0.63 (s,3H), 1.07 (s,3H), 1.34 (s,3H), 1.52 (s,3H) and 4.18 (s,2H).

EXAMPLE 9

(2β,3α,5α)-3,21-dihydroxy-2-(2,2-dimethyl-4-morpholinyl)pregnan-20-one 2,2-Dimethylmorpholine (3.0 g) was added to a stirred mixture (3:1) of (2α,3α,5α)-2,3-epoxy-21-hydroxypregnan-20-one cyclic 1,2-ethanediyl acetal and its 3α,4α-epoxy isomer (4.0 g) (prepared as described in U.S. Pat. No. 3,415,817) in 1,2-ethanediol (60 ml) and the mixture was heated under reflux in an atmosphere of nitrogen for 4 h. The mixture was poured into water (1 l) and the precipitated solid was filtered off and washed with water. The solid was dissolved in methanol (100 ml) and a solution of methanesulfonic acid (2.0 g) in methanol (50 ml) was added. This solution was stirred at 55° C. for 1 h and then poured into water (1 l). Aqueous sodium carbonate was added until the pH exceeded 9. The precipitated solid was filtered off, dissolved in dichloromethane and the solution was dried over sodium sulfate. The solvent was removed under reduced pressure and the residual solid was chromatographed on silica gel. The purified product was crystallised from acetone and then from methanol to give (2β,3α,5α)-3,21-dihydroxy-2-(2,2-dimethyl-4-morpholinyl)pregnan-20-one (1.40 g). m.p. 184°–186° C.

EXAMPLE 10

(2β,3α,5α)-acetyloxy)-3-hydroxy-2-(2,2-dimethyl-4-morpholinyl)pregnan-20-one

A solution of methanesulfonyl chloride (2.48 ml) in dry pyridine (9.6 ml) was added to a solution of the 3,21-dihydroxy compound of Example 9 (3.26 g) in dry pyridine (33 ml) at −25° C. over ca. 5 min. The solution was stirred at −25° C. for 1.5 h and poured into water (400 ml). Aqueous sodium carbonate was added until the pH exceeded 9 and the precipitated solid was filtered off and dissolved in dichloromethane. The solution was dried over sodium sulfate and the solvent was removed under reduced pressure to give (2β,3α,5α)-3-hydroxy-2-(2,2-dimethyl-4-morpholinyl)-21-[(methylsulfonyl)oxy]pregnan-20-one (3.80 g). δ (CDCl$_3$) 0.65 (s,3H), 0.86 (s,3H), 3.22 (s,3H) and 4.79 (m,2H).

Anhydrous potassium acetate (470 mg) was added to (2β,3α,5α)-3-hydroxy-2-(2,2-dimethyl-4-morpholinyl)-21-[(methylsulfonyl)oxy]pregnan-20-one (1.0 g) in ethanol (15 ml) and the solution was heated under reflux for 1.5 h. The reaction mixture was poured into water (150 ml) and the precipitated solid was filtered off, washed with water and the solid was dissolved in dichloromethane. After drying the solution over sodium sulfate, the solvent was removed under reduced pressure and the residue was chromatographed on silica gel. The purified product was crystallised from methanol to give (2β,3α,5α)-21-(acetyloxy)-3-hydroxy-2-(2,2-dimethyl-4-morpholinyl)pregnan-20-one (330 mg). m.p. 174°–175° C.; $[\alpha]_D$ +13.9° (c 0.5).

EXAMPLE 11

(2β,3α,5α)-3,21-dihydroxy-2-(2,2-dimethyl-4-morpholinyl)pregnan-20-one methanesulfonate (1:1) salt A solution of methanesulfonic acid (429 mg) in methanol (10 ml) was added to a solution of the (2β,3α,5α)-3,21-dihydroxy-2-(2,2-dimethyl-4-morpholinyl)pregnan-20-one of Example 9 (2.0 g) in methanol (20 ml). The solvent was removed under reduced pressure to afford (2β,3α,5α)-3,21-dihydroxy-2-(2,2-dimethyl-4-morpholinyl)pregnan-20-one methanesulfonate (1:1) salt (2.43 g). $[\alpha]_D$ +108.4° (c 0.6).

In a similar manner the following salt was prepared:

(2β,3α,5α)-21-(acetyloxy)-3-hydroxy-2-(2,2-dimethyl-4-morpholinyl)pregnan-20-one methanesulfonate (1:1) salt, with the 21-(acetyloxy) compound of Example 10 as starting material. $[\alpha]_D$ +113.3° (c 0.5).

EXAMPLE 12

(2β,3α,5α)-3-hydroxy-3-hydroxy-2-(2,2-dimethyl-4-morpholinyl)pregnan-20-one 2,2-Dimethylmorpholine (10.8 g) was added to a stirred mixture (3:1) of (2β,3α,5α)-2,3-epoxypregnan-20-one cyclic 1,2-ethanediyl acetal and its 3α,4α-epoxy isomer (7.0 g) (prepared as described in British patent 1,039,441) in 1,2-ethanediol (100 ml) and the mixture was heated under reflux in an atmosphere of nitrogen for 2 h. The reaction mixture was poured into water (1 l) and the precipitated solid was filtered off and washed with water. The solid was dissolved in methanol (200 ml) and a solution of methanesulfonic acid (5.5 g) in methanol (50 ml) was added. This solution was stirred at room temperature for 1 h, and then reduced in volume in vacuo to ca. 50 ml. Aqueous sodium carbonate was added until the pH exceeded 9 and the mixture was poured into water (1 l). The precipitated solid was filtered off and then dissolved in dichloromethane. After drying the solution over sodium sulfate, the solvent was removed under reduced pressure. The solid residue was chromatographed on silica gel and the purified product was crystallised from methanol to give (2β,3α,5α)-3-hydroxy-2-(2,2-dimethyl-4-morpholinyl)pregnan-20-one (3.45 g). m.p. 174°–175.5° C.

In a similar manner the following alkylated morpholine derivatives were prepared, differing only in that other substituted morpholine derivatives were used:

with (rac)-2-methylmorpholine a mixture was obtained of (i) and (ii):
- (i) (2β,3α,5α)-3-hydroxy-2-[(2R)-methyl-4-morpholinyl]pregnan-20-one. m.p. 196°–198° C.; $[\alpha]_D$ +151.5° (c 0.8).
- (ii) (2β,3α,5α)-3-hydroxy-2-[(2S)-methyl-4-morpholinyl]pregnan-20-one. m.p. 163°–167° C.; $[\alpha]_D$ +160° (c 1.0).

The mixture of (i) and (ii) was separated by fractional crystallisation from methanol and from acetone-hexane.

with (rac)-2-ethylmorpholine a mixture was obtained of (iii) and (iv):
- (iii) (2β,3α,5α)-2-[(2R)-ethyl-4-morpholinyl]-3-hydroxypregnan-20-one. m.p. 190°–192° C.; $[\alpha]_D$ +151.8° (c 0.9).
- (iv) (2β,3α,5α)-2-[(2S)-ethyl-4-morpholinyl]-3-hydroxypregnan-20-one. m.p. 120.5°–122° C.; $[\alpha]_D$ +156.6° (c 0.6).

The mixture of (iii) and (iv) was separated by fractional crystallisation from acetone.

with (+)-2-phenylmethylmorpholine:
- (v) (2β,3α,5α)-3-hydroxy-2-[(2R)-phenylmethyl-4-morpholinyl]pregnan-20-one. δ (CDCl$_3$) 0.61 (s,3H), 0.83 (s,3H), 2.12 (s,3H) and 7.15–7.38 (m,5H).

with (−)-2-phenylmethylmorpholine:
- (vi) (2β,3α,5α)-3-hydroxy-2-[(2S)-phenylmethyl-4-morpholinyl]pregnan-20-one. δ (CDCl$_3$) 0.60 (s,3H), 0.80 (s,3H), 2.12 (s,3H) and 7.12–7.35 (m,5H).

with 2,2,-diethylmorpholine (prepared similar to the method described for (2R)-methylmorpholine hydrochloride in Example 16, using 2,2-diethyloxirane as starting material:
- (vii) (2β,3α,5α)-2-(2,2-diethyl-4-morpholinyl)-3-hydroxypregnan-20-one. δ (CDCl$_3$) 0.62 (3H,s), 0.88 (s,3H) and 2.10 (s,3H).

with 2,6-dimethylmorpholine a mixture was obtained of a cis- and two trans-2,6-dimethyl-4-morpholinyl isomers from which (viii) and (ix) were separated by crystallisation of the hydrochloride salts from diethyl ether and then by crystallisation of the free bases from methanol:
- (viii) (2β,3α,5α)-3-hydroxy-2-(cis-2,6-dimethyl-4-morpholinyl)pregnan-20-one. δ (CDCl$_3$) 0.57 (s,3H), 1.05 (s,3H), 1.14 (d, J 6.4 Hz, 3H),1.19 (d, J 6.4 Hz, 3H) and 2.11 (s,3H).
- (ix) (2β,3α,5α)-3-hydroxy-2-(trans-2,6-dimethyl-4-morpholinyl)pregnan-20-one.

EXAMPLE 13

(2β,3α,5α)-21-chloro-3-hydroxy-3-2-[(2R)-methyl-4-morpholinyl]pregnan-20-one

The (2R)-methyl-4-morpholinyl compound of Example 12(i) (1.61 g), 2-aminoethanol (8 ml), toluene (40 ml) and Dowex 50-W resin (160 mg) were added to a flask fitted with a water separator. The mixture was heated under reflux for 7 h, whereupon approximately 7 ml of distillate had collected in the water separator. The contents of the flask were filtered while still hot and the cooled residue was rinsed with diethyl ether. The filtrate was washed with water, dried over sodium sulfate and the solvent was removed under reduced pressure. Crystallisation of the residue from diethyl ether afforded (2β,3α,5α)-20-[(2-hydroxyethyl)imino]-2-[(2R)-methyl-4-morpholinyl]pregnan-3-ol. m.p. 162°–165° C.; $[\alpha]_D$ +111.6° (c 0.75).

N-Chlorosuccinimide (348 mg) was added to a suspension of (2β,3α,5α)-20-[(2-hydroxyethyl)imino]-2-[(2R)-methyl-4-morpholinyl]pregnan-3-ol (1.19 g) in tetrahydrofuran (24 ml). The resulting solution was stirred at room temperature for 2 h and hydrochloric acid (7.7 ml; 1M) was then added. After stirring at room temperature for 2 h the reaction mixture was poured into water (150 ml). Aqueous sodium carbonate was added until the pH exceeded 9 and the precipitated solid was filtered off, washed with water and dissolved in dichloromethane. After drying over sodium sulfate, the solvent was removed under reduced pressure and the residue was crystallised from methanol to give (2β,3α,5α)-21-chloro-3-hydroxy-2-[(2R)-methyl-4-morpholinyl]pregnan-20-one (0.855 g). m.p. 191°–198° C. (dec); $[\alpha]_D$ +161° (c 0.69).

EXAMPLE 14

(2β,3α,5α)-3-hydroxy-2-(2,2-dimethyl-4-morpholinyl)pregnan-20-one 2-hydroxy-1,2,3-propanetricarboxylate (1:1) salt A solution of citric acid (141 mg) in methanol (20 ml) was added to a solution of the 2-(2,2-dimethyl-4-morpholinyl) compound of Example 12 (290 mg) in methanol (20 ml). The solvent was removed under reduced pressure to afford (2β,3α,5α)-3-hydroxy-2-(2,2-dimethyl-4-morpholinyl)-pregnan-20-one 2-hydroxy-1,2,3-propanetricarboxylate (1:1) salt (430 mg). $[\alpha]_D$ +99.5° (c 1.0).

In a similar manner the following salts were prepared:

(i) (2β,3α,5α)-3-hydroxy-2-(2,2-dimethyl-4-morpholinyl)pregan-20-one methanesulfonate (1:1) salt, using the 2-(2,2-dimethyl-4-morpholinyl) compound of Example 12 and methanesulfonic acid as starting materials. m.p. 212°–213° C.; $[\alpha]_D$ +113.2° (c 0.6).

(ii) (2β,3α,5α)-3-hydroxy-2-[(2R)-2-methyl-4-morpholinyl]pregnan-20-one methanesulfonate (1:1) salt, using the (2R)-2-methyl-4-morpholinyl compound of Example 12(i) and methanesulfonic acid as starting materials. m.p. 230° C. (dec); $[\alpha]_D$ +121.5° (c 0.83).

(iii) (2β,3α,5α)-3-hydroxy-2-[(2S)-2-methyl-4-morpholinyl]pregnan-20-one methanesulfonate (1:1) salt, using the (2S)-methyl-4-morpholinyl compound of Example 12(ii) and methanesulfonic acid as starting materials. m.p. 111°–115° C.

(iv) (2β,3α,5α)-2-[(2R)-ethyl-4-morpholinyl]-3-hydroxypregnan-20-one 2-hydroxy-1,2,3-propanetricarboxylate (1:1) salt, using the (2R)-ethyl-4-morpholinyl compound of Example 12(iii) and citric acid as starting materials. $[\alpha]_D$ +107.7° (c 1.0).

(v) (2β,3α,5α)-2-[(2S)-ethyl-4-morpholinyl]-3-hydroxypregnan-20-one 2-hydroxy-1,2,3-propanetricarboxylate (1:1) salt, using the (2S)-ethyl-4-morpholinyl compound of Example 12(iv) and citric acid as starting materials. $[\alpha]_D$ +113.2° (c 0.8).

(vi) (2β,3α,5α)-3-hydroxy-2-[(2R)-phenylmethyl-4-morpholinyl]pregnan-20-one methanesulfonate (1:1) salt, using the (2R)-phenylmethyl-4-morpholinyl compound of Example 12(v) and methanesulfonic acid as starting materials. m.p. 208°–210° C.; $[\alpha]_D$ +113.3° (c 1.3).

(vii) (2β,3α,5α)-3-hydroxy-2-[(2S)-phenylmethyl-4-morpholinyl]pregnan-20-one methanesulfonate (1:1) salt, using the (2S)-phenylmethyl-4-morpholinyl compound of Example 12(vi) and methanesulfonic acid as starting materials. $[\alpha]_D$ +105.6° (c 1.0).

(viii) (2β,3α,5α)-2-(2,2-diethyl-4-morpholinyl)-3-hydroxypregnan-20-one 2-hydroxy-1,2,3-propane-tricarboxylate (1:1) salt, using the 2-(2,2-diethyl-4-morpholinyl) compound of Example 12(vii) and citric acid as starting materials. δ (CDCl$_3$) 0.63 (s,3H) and 2.12 (s,3H).

(ix) (2β,3α,5α)-3-hydroxy-2-(cis-2,6-dimethyl-4-morpholinyl)pregnan-20-one hydrochloride (1:1) salt, using the 2-(cis-2,6-dimethyl-4-morpholinyl) compound of Example 12(viii) and hydrochloric acid as starting materials. m.p. 228°–235° C.; $[\alpha]_D$ +143.9° (c 0.9).

(x) (2β,3α,5α)-3-hydroxy-2-(trans-2,6-dimethyl-4-morpholinyl)pregnan-20-one methanesulfonate (2:3) salt (isomer A), using the 2-(trans-2,6-dimethyl-4-morpholinyl) compound of Example 12(ix) and methanesulfonic acid as starting materials. δ (CDCl$_3$) 0.63 (s,3H), 0.93 (s,3H), 1.25 (d,3H), 1.60 (d,3H), 2.12 (s,3H) and 2.85 (s,3H).

(xi) (2β,3α,5α)-21-chloro-3-hydroxy-2-[(2R)-methyl-4-morpholinyl]pregnan-20-one methanesulfonate (1:1) salt, using the 21-chloro-2-[(2R)-methyl-4-morpholinyl] compound of Example 13 and methanesulfonic acid as starting materials. m.p. 205°–207° C.; $[\alpha]_D$ +131.7° (c 0.8).

EXAMPLE 15

Injection formulations

| | |
|---|---|
| (a) compound of Example 6 | 10–50 mg/ml |
| hydrogen chloride | q.s. to pH 3 |
| sodium chloride | q.s. to isotonic |
| water for injections | to 1 ml |
| (b) compound of Example 6 | 10–50 mg/ml |
| sodium acetate trihydrate | 2.26 mg |
| acetic acid | 5.0 mg |
| hydrogen chloride or sodium hydroxide | q.s. to pH 4–5 |
| sodium chloride | q.s. to isotonic |
| water for injections | to 1 ml |
| (c) compound of Example 6 | 10–50 mg/ml |
| disodium monohydrogen phosphate | 5 mg |
| phosphoric acid or sodium hydroxide | q.s. to pH 6–8 |
| sodium chloride | q.s. to isotonic |
| water for injections | to 1 ml |

(d), (e) and (f): as (a), (b) and (c) wherein sodium chloride is replaced by mannitol, after which the product is freeze-dried.

EXAMPLE 16

(2β,3α,5α)-3-hydroxy-2-[(2R)-methyl-4-morpholinyl]pregnane-11,20-dione (2R)-Methylmorpholine hydrochloride.

(R)-Methyloxirane (23 g) (prepared by the method described by K. Rossen et al., Synth. Commun., 1993, 23, 1071) was added dropwise over 1 h to a stirred solution of 2-aminoethanol (96 ml) in water (65 ml) at 4° C. The mixture was stirred for a further 1.5 h at 4° C. and then for 17 h at ambient temperature. Removal of the water and excess 2-aminoethanol under reduced pressure and distillation of the residue in vacuo afforded (R)-1-[2-(hydroxyethyl)amino]-2-propanol (36.8 g). b.p. 106°–112° C. (0.5 mmHg); $[\alpha]_D$ −44.5° (c 0.7). (2R)-Methylmorpholine hydrochloride [δ (C$_5$D$_5$N) 1.08 (d, J 6.2 Hz, 3H), 2.93 (dd, J 12.6, 11.0 Hz, 1H), 3.24 (dt, J 12.4, 4.2 Hz, 1H), 3.54 (m, 2H), 3.96 (m, 1H) and 4.26 (m, 2H)] was prepared from the foregoing (R)-1-[2-(hydroxyethyl)amino]-2-propanol according to the method described for 2,2-dimethylmorpholine in Example 1. (2R)-Methylmorpholine hydrochloride (7.5 g) and powdered sodium hydroxide (2.18 g) were added to a stirred mixture (3.5:1) of (2α,3α,5α)-2,3-epoxypregnane-11,20-dione 20-cyclic 1,2-ethanediyl acetal and its 3α,4α-epoxy isomer (5.0 g) (prepared as described in British patent 1,039,441) in 1,2-ethanediol (50 ml) and the mixture was heated at 110° C. for 20 h. The reaction mixture was poured into water (500 ml) and the precipitated solid was filtered off and washed with water. The solid was suspended in methanol (45 ml) and methanesulfonic acid (1.7 ml) and water (10 ml) were added. The resulting mixture was stirred at ambient temperature for 45 min, diluted with water and then extracted with ethyl acetate. Aqueous sodium hydroxide (4M) was added to the aqueous phase until the pH exceeded 9. The precipitated solid was filtered off, dissolved in dichloromethane and the solution was washed with water. After drying over sodium sulfate the solvent was removed under reduced pressure. The solid residue (3.78 g) was crystallised from diethyl ether and the purified product (3.17 g) was recrystallised from dichloromethane-diethyl ether to give (2β,3α,5α)-3-hydroxy-2-[(2R)-methyl-4-morpholinyl]pregnane-11,20-dione (2.34 g). Om.p. 180°–182° C.; $[\alpha]_D$ +136.5° (c 0.7).

The following compounds were prepared in a similar manner using 2-substituted amines prepared in a similar manner as described for the preparation of 2,2-dimethylmorpholine:

(i) (2β,3α,5α)-3-hydroxy-2-[(2R)-ethyl-4-morpholinyl]pregnane-11,20-dione. m.p. 188°–191° C.; $[\alpha]_D$ +130.4° (c 0.5).

(ii) (2β,3α,5α)-3-hydroxy-2-[(2S)-ethyl-4-morpholinyl]pregnane-11,20-dione. m.p. 85°–86° C.; $[\alpha]_D$ +140° (c 0.6).

The mixture of (i) and (ii), prepared from racemic 2-ethylmorpholine, was crystallised from acetone-heptane to give (i). The isomer (ii) was obtained by chromatography of the mother liquor and then crystallisation of the oxalate salt from ethanol-diethyl ether.

(iii) (2β,3α,5α)-3-hydroxy-2-(2,2-dibutyl-4-morpholinyl)pregnane-11,20-dione. m.p. 159.5°–162.5° C.; $[\alpha]_D$+109.2° (c 0.5).

EXAMPLE 17

(2β,3α,5α)-3-hydroxy-2-(2,2-diphenyl-4-morpholinyl)pregnane-11,20-dione 2,2-Diphenylmorpholine (5.97 g) (G. E. M. Moussa et al, Indian J.Chem. Sect. B., 1980, 19, 798) was added to a stirred mixture (3.5:1) of (2α,3α,5α)-2,3-epoxypregnane-11,20-dione 20-cyclic 1,2-ethanediyl acetal and its 3α,4α-epoxy isomer (3.74 g) prepared as described in British patent 1,039,441) in 1,2-ethanediol (37 ml). The reaction mixture was heated at 125° C. for 24 h in an atmosphere of nitrogen and then the temperature was increased to 140° C. for 24 h. The mixture was then heated under reflux for 24 h before water (2 ml) was added. After boiling for a further 24 h, the mixture was poured into water and extracted with diethyl ether. The organic phase was extracted with hydrochloric acid (1M) and the aqueous phase was treated with sodium carbonate until the pH exceeded 9. After extracting with diethyl ether, the organic phase was dried over sodium sulfate and the solvent was removed under reduced pressure. The resulting oil was chromatographed on silica gel and the purified product was successively crystallised from diethyl ether and methanol to give (2β,3α,5α)-3-hydroxy-2-(2,2-diphenyl-4-morpholinyl)pregnane-11,20-dione (643 mg). m.p. 248°–250° C.; $[\alpha]_D$ +166.2° (c 0.7).

EXAMPLE 18

(2β,3α,5α)-2-[(2S)-phenylmethyl-4-morpholinyl]-3-hydroxypregnane-11,20-dione (−)-2-Phenylmethylmorpholine (4.3 g) (G. R. Brown et al, J. Pharm. Pharmacol., 1990, 42, 797) was added to a stirred mixture (3.5:1) of (2α,3α,5α)-2,3-epoxypregnane-11,20-dione 20-cyclic 1,2-ethanediyl acetal and its 3α,4α-epoxy isomer (3.03 g) (prepared as described in British patent 1,039,441) in 1,2-ethanediol (30 ml). The reaction mixture was heated at 115° C. for 24 h in an atmosphere of nitrogen, poured into water, extracted with t-butyl methyl ether and the organic phase was taken to dryness under reduced pressure. The residue was dissolved in methanol (45 ml) and to the stirred solution was added water (5 ml) and methanesulfonic acid (2.5 ml). After 1 h the solution was diluted with water and extracted with ethyl acetate. The aqueous phase was treated with sodium carbonate until the pH exceeded 9 and then extracted with ethyl acetate. The organic layer was washed with water, dried over sodium sulfate and the solvent was removed under reduced pressure. The residue was chromatographed on silica gel and the purified product was crystallised from methanol to give (2β,3α,5α)-2-[(2S)-phenylmethyl-4-morpholinyl]-3-hydroxypregnane-11,20-dione (2.03 g). m.p. 160°–161.5° C.; $[\alpha]_D$ +159° (c 0.6).

EXAMPLE 19

(2β,3α,5α)-2-[2(R)-phenylmethyl-4-morpholinyl]-3-hydroxypregnane-11,20-dione

The title compound was prepared by the method described for the 2(S)-phenylmethyl-4-morpholinyl diastereoisomer of Example 18 with the exception that (rac)-2-phenylmethylmorpholine (G. R. Brown et al., J. Pharm. Pharmacol., 1990, 42, 797) was used in place of the (−)-enantiomer. Crystallisation of the mixture of diastereoisomers from diethyl ether gave (2β,3α,5α)-2-[2(R)-phenylmethyl-4-morpholinyl]-3-hydroxypregnane-11,20-dione m.p. 170°–171.5° C.; $[\alpha]_D$ +91.6° (c 0.6).

EXAMPLE 20

(2β,3α,5α)-2-(2,2-diethyl-4-morpholinyl)-3-hydroxypregnane-11,20-dione 2,2-Diethylmorpholine hydrochloride (9.6 g) [prepared from the known 2,2-diethyloxirane (B. Rickborn et al, J. Am. Chem. Soc., 1971, 93, 1693) in a similar manner as for the preparation of 2,2-dimethylmorpholine of Example 1] was added to a stirred mixture (3.5:1) of (2α,3α,5α)-2,3-epoxypregnane-11,20-dione 20-cyclic 1,2-ethanediyl acetal and its 3α,4α-epoxy isomer (5.0 g) (prepared as described in British patent 1,039,441) in 1,2-ethanediol (50 ml). Powdered sodium hydroxide (2.14 g) was then added and the mixture was heated at 110° C. for 22 h and then poured into water (500 ml). The precipitated solid was filtered off, washed with water and suspended in a mixture of methanol (45 ml) and water (10 ml). Methanesulfonic acid (1.4 ml) was added and the resulting solution was stirred at room temperature for 45 min and then poured into water (500 ml). After extraction with ethyl acetate, aqueous sodium hydroxide (4M) was added to the aqueous phase until the pH exceeded 9. The precipitated solid was filtered off, washed with water and dissolved in dichloromethane. After washing the solution with water and drying over sodium sulfate, the solvent was removed under reduced pressure to afford an amorphous solid which was crystallised from diethyl ether to give (2β,3α,5α)-2-(2,2-diethyl-4-morpholinyl)-3-hydroxypregnane-11,20-dione (2.04 g). m.p. 177°–179° C.; $[\alpha]_D$ +126.0° (c 0.7).

EXAMPLE 21

(2β,3α,5α)-3-hydroxy-2-[4-(1-oxo-4-azaspiro[5.5]undecanyl)]pregnane-11,20-dione

1-Oxa-4-azaspiro[5.5]undecane (7 g) (J. M. McManus et al., J. Med. Chem., 1965, 8, 766) was added to a stirred mixture (9:1) of (2α,3α,5α)-2,3-epoxypregnane-11,20-dione 20-cyclic 1,2-ethanediyl acetal and its 3α,4α-epoxy isomer (4.0 g) (prepared as described in British patent 1,039,441) in 1,2-ethanediol (50 ml). The mixture was heated at 120°–125° C. for 23 h, poured into water (500 ml) and the mixture was extracted with diethyl ether. The organic phase was washed with water and then dried over sodium sulfate. The solvent was removed under reduced pressure and the residue was dissolved in a mixture of methanol (56 ml) and water (10 ml). Methanesulfonic acid (2.1 ml) was added and the solution was stirred at room temperature for 30 min and then poured into water (500 ml). After extraction with diethyl ether, aqueous sodium hydroxide (4M) was added to the aqueous phase until the pH exceeded 9 and the mixture was extracted with diethyl ether. The organic phase was washed with water, dried over sodium sulfate and the solvent was removed under reduced pressure. The resulting oil was chromatographed on silica gel and the purified product was crystallised from diethyl ether to give (2β,3α,5α)-3-hydroxy-2-[(4-(1-oxa-azaspiro[5.5]undecanyl)]pregnane-11,20-dione (2.8 g). m.p. 203°–205° C.; [α]$_D$ +120.0° (c 0.6).

EXAMPLE 22

(2β,3α,5α)-3-hydroxy-2-(2,2,6,6-tetramethyl-4-morpholinyl)pregnane-11,20-dione

Crude 2,2,6,6-tetramethylmorpholine hydrochloride (15.4 g) (E. Nowak in EP 252875) was added to a stirred mixture (9:1) of (2α,3α,5α)-2,3-epoxypregnane-11,20-dione 20-cyclic 1,2-ethanediyl acetal and its 3α,4α-epoxy isomer (5.0 g) (prepared as described in British patent 1,039,441) in 1,2-ethanediol (50 ml). Powdered sodium hydroxide (3.43 g) was added and the mixture was heated at 120°–125° C. for 22 h then poured into water (500 ml). This mixture was extracted with diethyl ether and the organic phase was washed with water. After drying over sodium sulfate, the solvent was removed under reduced pressure and the residue was dissolved in methanol (100 ml) and water (20 ml). Methanesulfonic acid (4 ml) was added and the solution was stirred at room temperature for 45 min and then poured into water (1 l). After extraction with diethyl ether, aqueous sodium hydroxide (4M) was added to the aqueous phase until the pH exceeded 9. The mixture was extracted with diethyl ether and the organic phase was washed with water. After drying over sodium sulfate, the solvent was removed under reduced pressure and the residue was chromatographed on silica gel. The purified product was crystallised from acetone-hexane to give (2β,3α,5α)-3-hydroxy-2-(2,2,6,6-tetramethyl-4-morpholinyl)pregnane-11,20-dione (361 mg). m.p. 212°–215° C.; [α]$_D$ +126.8° (c 0.5).

EXAMPLE 23

(2β,3α,5α)-3-hydroxy-2-[(2R)-methyl-4-morpholinyl]pregnane-11,20-dione methanesulfonate (1:1) salt A solution of methanesulfonic acid (445 mg) in ethanol (5 ml) was added to a suspension of (2β,3α,5α)-3-hydroxy-2-[(2R)-methyl-4-morpholinyl]pregnane-11,20-dione (2.0 g) in ethanol (20 ml). The solvent was removed under reduced pressure and the residue was crystallised from acetone-diethyl ether to give (2β,3α,5α)-3-hydroxy-2-[(2R)-methyl-4-morpholinyl]pregnane-11,20-dione methanesulfonate (1:1) salt (2.22 g). m.p. 230° C. (dec); [α]$_D$ +108.9° (c 0.8).

In a similar manner the following salts were prepared:
(i) (2β,3α,5α)-3-hydroxy-2-[(2R)-ethyl-4-morpholinyl]pregnane-11,20-dione methanesulfonate (1:1) salt, with the 2-ethylmorpholine compound of Example 16(i) as starting material. [α]$_D$ +112.7° (c 0.2).
(ii) (2β,3α,5α)-3-hydroxy-2-[(2S)-ethyl-4-morpholinyl]pregnane-11,20-dione methanesulfonate (1:1) salt, with the 2-ethylmorpholine compound of Example 16(ii) as starting material. [α]$_D$ +110° (c 0.6).

EXAMPLE 24

(2β,3α,5α)-3-hydroxy-2-(2,2-dibutyl-4-morpholinyl)pregnane-11,20-dione methanesulfonate (1:1) salt A solution of methanesulfonic acid (181 mg) in ethanol (7 ml) was added to a suspension of (2β,3α,5α)-3-hydroxy-2-(2,2-dibutyl-4-morpholinyl)pregnane-11,20-dione (1.0 g) in ethanol (3 ml). The resulting suspension was heated to effect solution and the solvent was removed under reduced pressure to give (2β,3α,5α)-3-hydroxy-2-(2,2-dibutyl-4-morpholinyl)pregnane-11,20-dione methanesulfonate (1:1) salt (1.06 g). [α]$_D$ +86.3° (c 0.7).

In a similar manner the following salts were prepared:
(i) (2β,3α,5α)-3-hydroxy-2-(2,2-diphenyl-4-morpholinyl)pregnane-11,20-dione methanesulfonate (1:1) salt, with the 2,2-diphenylmorpholine compound of Example 17 as starting material. [α]$_D$ −23.1° (c 0.5).
(ii) (2β,3α,5α)-2-(2,2-diethyl-4-morpholinyl)-3-hydroxypregnane-11,20-dione methanesulfonate (1:1) salt, with the 2,2-diethylmorpholine compound of Example 20 as starting material. [α]$_D$ +97.7° (c 0.7).
(iii) (2β,3α,5α)-3-hydroxy-2-[4-(1-oxa-4-azaspiro [5.5] undecanyl)]pregnane-11,20-dione methanesulfonate (1:1) salt, with the 2-spirocyclohexylmorpholine compound of Example 21 as starting material. [α]$_D$ +98.1° (c 0.8).

EXAMPLE 25

(2β,3α,5α)-3-hydroxy-2-(2,2,6,6-tetramethyl-4-morpholinyl)pregnane-11,20-dione methanesulfonate (1:1) salt A solution of methanesulfonic acid (63 mg) in methanol (5 ml) was added to a suspension of (2β,3α,5α)-3-hydroxy-2-(2,2,6,6-tetramethyl-4-morpholinyl)pregnane-11,20-dione (311 mg) in methanol (5 ml). The solvent was removed under reduced pressure and the residue was crystallised from diethyl ether to give (2β,3α,5α)-3-hydroxy-2-(2,2,6,6-tetramethyl-4-morpholinyl)pregnane-11,20-dione methanesulfonate (1:1) salt (354 mg). m.p. 211°–217° C. (dec); [α]$_D$ +109.7° (c 0.6).

EXAMPLE 26

(2β,3α,5α)-3-hydroxy-2-[(2S)-phenylmethyl-4-morpholinyl]pregnane-11,20-dione 2-hydroxy-1,2,3-propanetricarboxylate (1:1) salt A solution of citric acid (766 mg) in methanol (20 ml) was added to a solution of (2β,3α,5α)-3-hydroxy-2-[(2S)-phenylmethyl-4-morpholinyl]pregnane-11,20-dione (2.03 g) in methanol (80 ml). The solvent was removed under reduced pressure to give (2β,3α,5α)-3-hydroxy-2-[(2S)-phenylmethyl-4-morpholinyl]pregnane-11,20-dione 2-hydroxy-1,2,3-propanetricarboxylate (1:1) salt (2.8 g). $[\alpha]_D$ +120.0° (c 0.7).

In a similar manner the following salts were prepared:

(i) (2β,3α,5α)-3-hydroxy-2-[(2R)-phenylmethyl-4-morpholinyl]pregnane-11,20-dione 2-hydroxy-1,2,3-propanetricarboxylate (1:1) salt, with the 2-phenylmethylmorpholine compound of Example 19 as starting material. $[\alpha]_D$ +86.0° (c 0.7).

(ii) (2β,3α,5α)-2-(2,2-diethyl-4-morpholinyl)-3-hydroxypregnane-11,20-dione 2-hydroxy-1,2,3-propanetricarboxylate (1:1) salt, with the 2,2-diethylmorpholine compound of Example 20 as starting material. $[\alpha]_D$ +90.9° (c 1.0).

EXAMPLE 27

(2β,3α,5α)-3-hydroxy-2-(2,2-dimethyl-4-thiomorpholinyl)pregnane-11,20-dione 2,2-Dimethylthiomorpholine (40 ml) (J. M. McManus et al., J. Med. Chem., 1965, 8, 766) was added to a stirred mixture (3.5:1) of (2α,3α,5α)-2,3-epoxypregnane-11,20-dione cyclic 1,2-ethanediyl acetal and its 3α,4α-epoxy isomer (8.0 g) (prepared as described in British patent 1,039,441) in 1,2-ethanediol (160 ml). The reaction mixture was heated at 125° C. for 5 h in an atmosphere of nitrogen and then poured into aqueous sodium chloride (1.6 l). The precipitated solid was filtered off, washed with water and dissolved in a mixture of methanol (160 ml) and dichloromethane (5–10 ml). After adding water (10 ml) and methanesulfonic acid (3 ml), the solution was stirred for 45 min and then concentrated under reduced pressure. Water was added and the mixture was extracted with ethyl acetate. The aqueous phase was treated with sodium carbonate until the pH exceeded 9 and then extracted with ethyl acetate. The organic layer was dried over sodium sulfate and the solvent was removed under reduced pressure. The product was crystallised from dichloromethane-methanol to give (2β,3α,5α)-3-hydroxy-2-(2,2-dimethyl-4-thiomorpholinyl)pregnane-11,20-dione (1.88 g). m.p. 201.5°–203° C.; $[\alpha]_D$ +149.7° (c 0.6).

EXAMPLE 28

(2β,3α,5α)-hydroxy-2-(2,2-dimethyl-4-thiomorpholinyl)pregnan-20-one 2,2-Dimethylthiomorpholine (10 ml) (J. M. McManus et al, J. Med. Chem., 1965, 8, 766) was added to a stirred mixture (3:1) of (2α,3α,5α)-2,3-epoxypregnan-20-one cyclic 1,2-ethanediyl acetal and its 3α,4α-epoxy isomer (2.5 g) (prepared as described in British patent 1,039,441) in 1,2-ethanediol (50 ml). The reaction mixture was heated under reflux for 7 h then poured into aqueous sodium chloride (800 ml). The precipitated solid was filtered off and washed with water. After dissolution in methanol (200 ml) and the addition of water (2 ml) and methanesulfonic acid (2.0 g), the solution was stirred for 45 min and then concentrated under reduced pressure. The resulting solution was diluted with water and treated with sodium carbonate until the pH exceeded 9. The precipitated solid was filtered off, dissolved in dichloromethane, dried over sodium sulfate and the solvent was removed under reduced pressure. The residual solid was chromatographed on silica gel and the purified product was crystallised from methanol to give (2β,3α,5α)-3-hydroxy-2-(2,2-dimethyl-4-thiomorpholinyl)pregnan-20-one (672 mg). m.p. 184°–185° C.; $[\alpha]_D$ −96.2° (c 0.9).

EXAMPLE 29

(2β,3α,5α)-hydroxy-2-(2,2-dimethyl-4-thiomorpholinyl)pregnane-11,20-dione 2-hydroxy-1,2,3-propanetricarboxylate (1:1) salt A solution of citric acid (576 mg) in methanol (70 ml) was added to (2β,3α,5α)-3-hydroxy-2-(2,2-dimethyl-4-thiomorpholinyl)pregnane-11,20-dione (1.39 g). The mixture was warmed to effect solution and the solvent was removed under reduced pressure to give (2β,3α,5α)-3-hydroxy-2-(2,2-dimethyl-4-thiomorpholinyl)pregnane-11,20-dione 2-hydroxy-1,2,3-propanetricarboxylate (1:1) salt (1.96 g). $[\alpha]_D$ +92.2° (c 0.5).

EXAMPLE 30

(2β,3α,5α)-3-hydroxy-2-(2,2-dimethyl-4-thiomorpholinyl)pregnan-20-one methanesulfonate (1:1) salt A solution of methanesulfonic acid (100 mg) in methanol (20 ml) was added to a solution of (2β,3α,5α)-3-hydroxy-2-(2,2-dimethyl-4-thiomorpholinyl)pregnan-20-one (464 mg) in methanol (30 ml). The solvent was removed under reduced pressure and the residue was crystallised from acetone to give (2β,3α,5α)-3-hydroxy-2-(2,2-dimethyl-4-thiomorpholinyl)pregnan-20-one methanesulfonate (1:1) salt (337 mg). m.p. 171°–177° C.; $[\alpha]_D$ +104.6° (c 0.9).

EXAMPLE 31

(2β,3α,5α,11β)-3,11-dihydroxy-2-(2,2-dimethyl-4-morpholinyl)pregnan-20-one 2,2-Dimethylmorpholine hydrochloride (120 g) was added to a stirred mixture (3.5:1) of (2α,3α,5α)-2,3-epoxypregnane-11,20-dione 20-cyclic 1,2-ethanediyl acetal and its 3α,4α-epoxy isomer (20 g) (prepared as described in British patent 1,039,441) in 1,2-ethanediol (400 ml). Anhydrous sodium carbonate (42 g) was then added cautiously and the mixture was heated at 60°–70° C. until effervescence had subsided. The mixture was heated further at 120°–130° C. for 4.5 h and then poured into water (4 l). The precipitated solid was filtered off, washed with water and dried in vacuo. A portion (2.5 g) of the resulting solid (A) was suspended in stirred ethanol (25 ml) and sodium borohydride (2.25 g) was added portionwise. The mixture was stirred for 15 h at room temperature, poured into water (250 ml) and the precipitated solid was filtered off, washed with water and dissolved in methanol (25 ml). Methanesulfonic acid (1.0 ml) was added and the solution was stirred at room temperature for 1 h and then poured into water (250 ml). After extraction with dichloromethane, sodium carbonate was added to the aqueous phase until the pH exceeded 9. The resulting mixture was extracted with dichloromethane and the organic phase was washed with water and dried over sodium sulfate. The solvent was removed under reduced pressure to afford a gum which was crystallised from diethyl ether to give (2β,3α,5α,11β)-3,11-dihydroxy-2-(2,2-dimethyl-4-morpholinyl)pregnan-20-one (755 mg). m.p. 224°–228° C.; $[\alpha]_D$ +136.4° (c 0.14).

EXAMPLE 32

(2β,3α,5α,11α)-3,11-hydroxy-2-(2,2-dimethyl-4-morpholinyl)pregnan-20-one

A portion (4.0 g) of the solid (A) of Example 31 was dissolved in ethanol (140 ml) and sodium (8.5 g) was added portionwise over 4 h. The mixture was poured into water (1.4 l) and the precipitated solid was filtered off, washed with water and dissolved in methanol (40 ml). Methanesulfonic acid (1.6 ml) was added and the solution was stirred at room temperature for 1 h and then poured into water (400 ml). After extraction with ethyl acetate, sodium carbonate was added to the aqueous phase until the pH exceeded 9. The resulting mixture was extracted with dichloromethane and the organic phase was washed with water. After drying over sodium sulfate, the solvent was removed under reduced pressure and the residue was chromatographed on silica gel. The purified product was crystallised from diethyl ether to give (2β,3α,5α,11α)-3,11-dihydroxy-2-(2,2-dimethyl-4-morpholinyl)pregnan-20-one (750 mg). m.p. 182°–185° C.; $[\alpha]_D$ +125.6° (c 0.25).

EXAMPLE 33

(2β,3α,5α11β)-3,11-dihydroxy-2-(2,2-dimethyl-4-morpholinyl)pregnan-20-one 2-hydroxy-1,2,3-propanetricarboxylate (1:1) salt A solution of citric acid (92 mg) in methanol (3 ml) was added to a suspension of (2β,3α,5α,11β)-3,11-dihydroxy-2-(2,2-dimethyl-4-morpholinyl)pregnan-20-one (213 mg) in methanol (2 ml). The resulting solution was taken to dryness under reduced pressure to give (2β,3α,5α,11β)-3,11-dihydroxy-2-(2,2-dimethyl-4-morpholinyl)pregnan-20-one 2-hydroxy-1,2,3-propanetricarboxylate (1:1) salt. $[\alpha]_D$ +119° (c 0.3).

In a similar manner the following salt was prepared:

(2β,3α,5α,11α)-3,11-dihydroxy-2-(2,2-dimethyl-4-morpholinyl)pregnan-20-one 2-hydroxy-1,2,3-propanetricarboxylate (1:1) salt with the 11α-hydroxy compound of Example 32 as starting material. $[\alpha]_D$ +90.6° (c 0.6).

EXAMPLE 34

(2β,3α,5α)-3-hydroxy-2-(2,2-dimethyl-4-morpholinyl)-21-thiocyanatopregnan-20-one To a mixture of (2β,3α,5α)-21-chloro-3-hydroxy-2-(2,2-dimethyl-4-morpholinyl)pregnan-20-one methanesulfonate (1:1) salt (1.5 g) in methanol (63 ml) was added a solution of potassium thiocyanate (5.14 g) in water (32 ml). The resulting solution was stirred at room temperature for 72 h, then poured into water and sodium carbonate was added until the pH exceeded 9. The precipitated solid was filtered off, washed with water and dissolved in dichloromethane. The solution was dried over sodium sulfate and the solvent was removed under reduced pressure. The residue was chromatographed on silica gel and the purified product was crystallised from methanol and then from diethyl ether to give (2β,3α,5α)-3-hydroxy-2-(2,2-dimethyl-4-morpholinyl)-21-thiocyanatopregnan-20-one (497 mg). m.p. 165.5°–166.5° C.; $[\alpha]_D$ +121.1° (c 1.3).

EXAMPLE 35

(2β,3α,5α)-3-hydroxy-2-(2,2-dimethyl-4-morpholinyl)-21-thiocyanatopregnane-11,20-dione To (2β,3α,5α)-21-chloro-3-hydroxy-2-(2,2-dimethyl-4-morpholinyl)pregnane-11,20-dione (3.1 g) was added a solution of methanesulfonic acid (615 mg) in methanol (63 ml) and then a solution of potassium thiocyanate (12.4 g) in water (32 ml). The resulting solution was stirred at room temperature for 24 h, poured into water and sodium carbonate was then added until the pH exceeded 9. The precipitated solid was filtered off, washed with water and dissolved in dichloromethane. This solution was dried over sodium sulfate and the solvent was removed under reduced pressure. The residue was chromatographed on silica gel and the purified product was crystallised from diethyl ether and then from methanol to give (2β,3α,5α)-3-hydroxy-2-(2,2-dimethyl-4-morpholinyl)-21-thiocyanatopregnane-11,20-dione (572 mg). m.p. 197°–198° C.; $[\alpha]_D$ +99.3° (c 0.8).

EXAMPLE 36

(2β,3α,5α)-21-azido-3-hydroxy-2-(2,2-dimethyl-4-morpholinyl)pregnane-11,20-dione A stirred mixture of (2β,3α,5α)-21-chloro-3-hydroxy-2-(2,2-dimethyl-4-morpholinyl)pregnane-11,20-dione (500 mg), sodium azide (140 mg), N,N-dimethylformamide (1.25 ml) in methanol (10 ml) and water (0.25 ml) was heated under reflux for 2 h, then cooled and poured into water (50 ml). The resulting precipitate was filtered off and dissolved in dichloromethane. After washing the solution with water and drying over sodium sulfate, the solvent was removed under reduced pressure and the residue (422 mg) was chromatographed on silica gel. The purified product was crystallised from dichloromethane-methanol to give (2β,3α,5α)-21-azido-3-hydroxy-2-(2,2-dimethyl-4-morpholinyl)pregnane-11,20-dione (176 mg). δ (CDCl$_3$) 0.62 (s,3H), 1.06 (s,3H), 1.22 (s,3H), 1.24 (s,3H) and 3.85 (s,2H).

EXAMPLE 37

(2β,3α,5α)-3-hydroxy-2-(2,2-dimethyl-4-morpholinyl)-11,20-dioxopregnane-21-carbonitrile A stirred mixture of (2β,3α,5α)-21-chloro-3-hydroxy-2-(2,2-dimethyl-4-morpholinyl)pregnane-11,20-dione (500 mg), sodium cyanide (500 mg), N,N-dimethylformamide (1.25 ml) in methanol (10 ml) and water (0.25 ml) was heated under reflux for 16 h. The resulting solution was cooled and poured into water (50 ml). The mixture was extracted with dichloromethane and the organic layer was washed with water to pH 7. After drying the solution over sodium sulfate, the solvent was removed under reduced pressure and the residue (430 mg) was chromatographed on silica gel. The purified product (208 mg) was crystallised from dichloromethane-methanol to give (2β,3α,5α)-3-hydroxy-2-(2,2-dimethyl-4-morpholinyl)-11,20-dioxopregnane-21-carbonitrile (96 mg). δ (CDCl$_3$) 0.62 (s, 3H), 1.06 (s,3H), 1.22 (s,3H), 1.26 (s,3H) and 3.38 (s,2H).

EXAMPLE 38

(2β,3α,5α)-3-hydroxy-2-(2,2-dimethyl-4-morpholinyl)-21-thiocyanatopregnan-20-one methanesulfonate (1:1) salt A solution of methanesulfonic acid (88 mg) in methanol (100 ml) was added to (2β,3α,5α)-3-hydroxy-2-(2,2-dimethyl-4-morpholinyl)-21-thiocyanatopregnan-20-one (445 mg) and the solvent was removed from the resulting solution to give (2β,3α,5α)-3-hydroxy-2-(2,2-dimethyl-4-morpholinyl)-21-thiocyanatopregnan-20-one methanesulfonate (1:1) salt (432 mg). [α]$_D$ +100.8° (c 0.4).

In a similar manner the following salts were prepared:
(i) (2β,3α,5α)-3-hydroxy-2-(2,2-dimethyl-4-morpholinyl)-21-thiocyanatopregnane-11,20-dione methanesulfonate (1:1) salt with the 21-thiocyanato compound of Example 35 as starting material [α]$_D$ +83.3° (c 0.5).
(ii) (2β,3α,5α)-21-azido-3-hydroxy-2-(2,2-dimethyl-4-morpholinyl)pregnane-11,20-dione methanesulfonate (1:1) salt with 21-azido compound of Example 36 as starting material [α]$_D$ +116.5° (c 0.9).
(iii) (2β,3α,5α)-3-hydroxy-2-(2,2-dimethyl-4-morpholinyl)-11,20-dioxopregnane-21-carbonitrile methanesulfonate (1:1) salt with the 21-cyano compound of Example 37 as starting material. δ (CDCl$_3$) 0.66 (s,3H), 1.09 (s,3H), 1.34 (s,3H), 1.52 (s,3H), 2.81 (s,3H), 3.42 (s,2H) and 4.27 (t,J 13 Hz, 1H).

EXAMPLE 39

(2β,3α,5α,17β)-3-hydroxy-2-(2,2-dimethyl-4-morpholinyl)androstane-17-carbonitrile 2,2-Dimethylmorpholine hydrochloride (2.43 g) and sodium hydroxide (640 mg) were added to a mixture of (2α,3α,5α,17β)-2,3-epoxyandrostane-17-carbonitrile (1.2 g) (prepared as described in British patent 1,434,919) in 1,2-ethanediol (12 ml) and the mixture was heated at 135° C. in an atmosphere of nitrogen for 24 h. The reaction mixture was poured into water (100 ml) and the precipitated solid was filtered off and then dissolved in dichloromethane. The solution was washed with water and dried over sodium sulfate. The solvent was removed under reduced pressure and the residue (1.55 g) was chromatographed on silica gel. The purified product (1.18 g) was crystallised from ether-heptane to give (2β,3α,5α,17β)-3-hydroxy-2-(2,2-dimethyl-4-morpholinyl)androstane-17-carbonitrile (903 mg). m.p. 170°–173° C.; [α]$_D$ +117.5° (c 0.8).

EXAMPLE 40

(2β,3α,5α,17β)-3-hydroxy-2-(2,2-dimethyl-4-morpholinyl)androstan-11-one-17-carbonitrile 2,2-Dimethylmorpholine hydrochloride (9.67 g) and sodium hydroxide (2.55 g) were added to a mixture (4:1) of (2α,3α,5α,17β)-2,3-epoxyandrostan-11-one-17-carbonitrile and its 3α,4α-epoxy isomer (5.0 g) (British patent 1,434, 919) in 1,2-ethanediol (50 ml) and the mixture was heated in an atmosphere of nitrogen at 120° C. for 19 h and then at 150° C. for 4.5 h. The reaction mixture was poured into water (500 ml) and the precipitated solid was filtered off and dissolved in dichloromethane. After washing the solution with water and drying over sodium sulfate, the solvent was removed under reduced pressure and the residue (6.9 g) was chromatographed on silica gel. The purified product (4.3 g) was sequentially crystallised from ethanol and acetone-diethyl ether to give (2β,3α,5α,17β)-3-hydroxy-2-(2,2-dimethyl-4-morpholinyl)androstan-11-one-17-carbonitrile (2.37 g). m.p. 206°–210° C.; [α]$_D$ +122.9° (c 0.8).

EXAMPLE 41

(2β,3α,5α,17β)-3-hydroxy-2-(2,2-dimethyl-4-morpholinyl)androstane-17-carbonitrile methanesulfonate (1:1) salt.

A solution of methanesulfonic acid (186 mg) in ethanol (2 ml) was added to a suspension of (2β,3α,5α,17β)-3-hydroxy-2-(2,2-dimethyl-4-morpholinyl)androstane-17-carbonitrile (800 mg) in ethanol (8 ml) and the mixture was stirred for 5 min. Removal of the solvent under reduced pressure afforded a solid which was precipitated from ethanol-diethyl ether to give (2β,3α,5α,17β)-3-hydroxy-2-(2,2-dimethyl-4-morpholinyl)androstane-17-carbonitrile methanesulfonate (1:1) salt (890 mg). [α]$_D$ +100.2° (c 0.2).

EXAMPLE 42

(2β,3α,5α,17β)-3-hydroxy-2-(2,2-dimethyl-4-morpholinyl)androstane-11-one-17-carbonitrile 2-hydroxy-1,2,3-propanetricarboxylate (1:1) salt A mixture of (2β,3α,5α,17β)-3-hydroxy-2-(2,2-dimethyl-4-morpholinyl)androstane-11-one-17-carbonitrile (500 mg) and citric acid (224 mg) in ethanol (5 ml) was stirred for 5 min. Removal of the solvent under reduced pressure and crystallisation from dichloromethane-diethyl ether afforded (2β,3α,5α,17β)-3-hydroxy-2-(2,2-dimethyl-4-morpholinyl)androstane-11-one-17-carbonitrile 2-hydroxy-1,2,3-propanetricarboxylate (1:1) salt (427 mg). [α]$_D$ +80.8° (c 0.5).

I claim:
1. A substituted 2β-morpholino-androstane derivative having the formula II

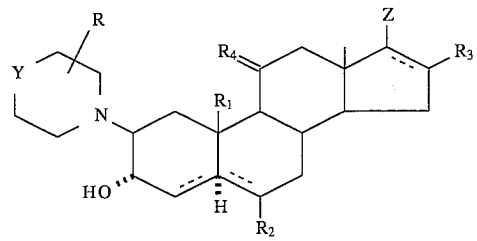

wherein
R represents one to four substituents, each one independently selected from (1–4C) alkyl, phenyl and benzyl, or two at the same carbon atom being together —(CH$_2$)$_n$— wherein n is 2–6;

$R_1$, $R_2$, and $R_3$ are independently H or methyl;

$R_4$ is H$_2$, (H, OH) or O;

Z is CN or COCH$_2$X;

X is selected from H, halogen, OH, CN, N$_3$, SCN, (1–6C) alkyl (optionally substituted by halogen), cyclohexyl, (1–6C) alkoxy, phenoxy, phenyl-(1–6C) alkoxy, (1–6C) acyloxy, (1–6C) acylthio, pyrrolidinyl, piperidinyl, morpholinyl, thiomorpholinyl and amino which is optionally substituted by (1–6C) alkyl;

Y is O or S;

and the dotted lines are optional bonds, H(5) being absent when the 4,5- or 5,6-linkage is a double bond;
or a pharmaceutically acceptable salt thereof.

2. A substituted 2β-morpholino-androstane derivative having formula III

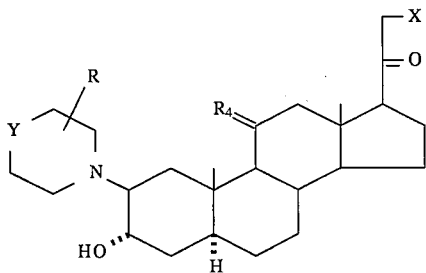

wherein

R represents one to four substituents independently selected from (1–4C) alkyl, phenyl and benzyl, or two substituents R are together —(CH$_2$)$_n$— wherein n is 2–6;

R$_4$ is H$_2$, (H,OH) or O;

X is selected from H, halogen, OH, CN, N$_3$, SCN, (1–6C) alkyl (optionally substituted by halogen), cyclohexyl, (1–6C) alkoxy, pyrrolidinyl, piperidinyl, morpholinyl, thiomorpholinyl and amino which is optionally substituted by (1–6C) alkyl; and Y is O or S;

or a pharmaceutically acceptable salt thereof.

3. The substituted 2β-morpholino-androstane derivative of claim 2 wherein X is H, Cl, OH, CN, N$_3$, SCN, C(1–6) acyloxy or C(1–6) acylthio, and Y is O.

4. The substituted 2β-morpholino-androstane derivative of claim 1 wherein R represents one or two methyl groups at the 2-position of the morpholino moiety.

5. The substituted 2β-morpholino-androstane derivative of claim 1 wherein R$_4$ is O.

6. The substituted 2β-morpholino-androstane derivative of claim 1 having the formula V

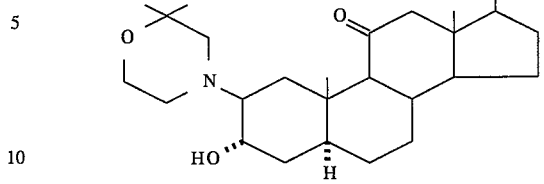

or a pharmaceutically acceptable salt thereof.

7. A process for the preparation of the substituted 2β-morpholino-androstane derivative of claim 1, comprising condensation of a substituted morpholine at the 2β-position of an androstane derivative by bringing together the substituted morpholine or a salt thereof and a 2,3-epoxyandrostane or 2,3-epoxy-19-nor-androstane derivative, which is suitably protected when necessary, after which the optionally present protective groups are removed, and the steroid obtained is isolated and purified.

8. A pharmaceutical composition comprising the substituted 2β-morpholino-androstane derivative of claim 1 and pharmaceutically suitable auxiliaries.

9. The process according to claim 7, further comprising introducing a substituent at the 21-position of the isolated and purified steroid.

10. A pharmaceutical composition comprising the substituted 2β-morpholino-androstane derivative of claim 1 and pharmaceutically suitable auxiliaries.

11. A pharmaceutical composition comprising the substituted 2β-morpholino-androstane derivative of claim 2 and pharmaceutically suitable auxiliaries.

12. A pharmaceutical composition comprising the substituted 2β-morpholino-androstane derivative of claim 6 and pharmaceutically suitable auxiliaries.

13. A method inducing anesthesia, comprising administering an effective amount of a substituted 2β-morpholino-androstane derivative of claim 1.

14. A method inducing anesthesia, comprising administering an effective amount of a substituted 2β-morpholino-androstane derivative of claim 2.

15. A method inducing anesthesia, comprising administering an effective amount of a substituted 2β-morpholino-androstane derivative of claim 6.

16. The substituted 2β-morpholino-androstane derivative of claim 2 wherein R represents one or two methyl groups at the 2-position of the morpholino moiety.

* * * * *